United States Patent
Kumar et al.

(10) Patent No.: US 10,195,564 B2
(45) Date of Patent: *Feb. 5, 2019

(54) BIO-CONVERSION OF REFINERY WASTE STREAMS

(71) Applicant: INDIAN OIL CORPORATION LIMIITED, Mumbai (IN)

(72) Inventors: Manoj Kumar, Faridabad (IN); Mahendra Pratap Singh, Faridabad (IN); Jayaraj Christopher, Faridabad (IN); Anurag Ateet Gupta, Faridabad (IN); Ravinder Kumar Malhotra, Faridabad (IN)

(73) Assignee: INDIAN OIL CORPORATION LIMIITED, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/088,094

(22) Filed: Mar. 31, 2016

(65) Prior Publication Data
US 2016/0296888 A1  Oct. 13, 2016

(30) Foreign Application Priority Data
Apr. 8, 2015 (IN) .......... 1467/MUM/2015

(51) Int. Cl.
| | | |
|---|---|---|
| *B01D 53/84* | (2006.01) |
| *C02F 3/34* | (2006.01) |
| *C12N 11/14* | (2006.01) |
| *C12P 7/62* | (2006.01) |
| *C10G 19/08* | (2006.01) |
| *C02F 103/10* | (2006.01) |
| *C02F 103/36* | (2006.01) |

(52) U.S. Cl.
CPC .............. *B01D 53/84* (2013.01); *C02F 3/341* (2013.01); *C02F 3/342* (2013.01); *C10G 19/08* (2013.01); *C12N 11/14* (2013.01); *C12P 7/62* (2013.01); *B01D 2251/95* (2013.01); *B01D 2255/804* (2013.01); *B01D 2257/504* (2013.01); *B01D 2258/0283* (2013.01); *C02F 2103/10* (2013.01); *C02F 2103/365* (2013.01); *Y02C 10/02* (2013.01)

(58) Field of Classification Search
None
See application file for complete search history.

(56) References Cited

U.S. PATENT DOCUMENTS

| | | |
|---|---|---|
| 5,244,756 A | 9/1993 | Mix et al. |
| 7,713,399 B2 | 5/2010 | Martinie et al. |
| 8,329,460 B2 | 12/2012 | Parent et al. |
| 8,329,498 B2 | 12/2012 | Hernandez |
| 8,480,796 B2 | 7/2013 | Fradette et al. |
| 2004/0040671 A1 | 3/2004 | Duesel, Jr. et al. |
| 2012/0107899 A1 | 5/2012 | Borchert et al. |
| 2013/0224842 A1 | 8/2013 | Parent et al. |

FOREIGN PATENT DOCUMENTS

| | | |
|---|---|---|
| CA | 2813640 A1 | 1/2003 |
| EP | 2354099 A1 | 8/2011 |
| WO | 2008095057 A2 | 8/2008 |

*Primary Examiner* — Thane Underdahl
(74) *Attorney, Agent, or Firm* — Maschoff Brennan

(57) ABSTRACT

The present invention relates to a process of conversion of waste streams of petroleum refinery into industrially useful products.

18 Claims, 1 Drawing Sheet

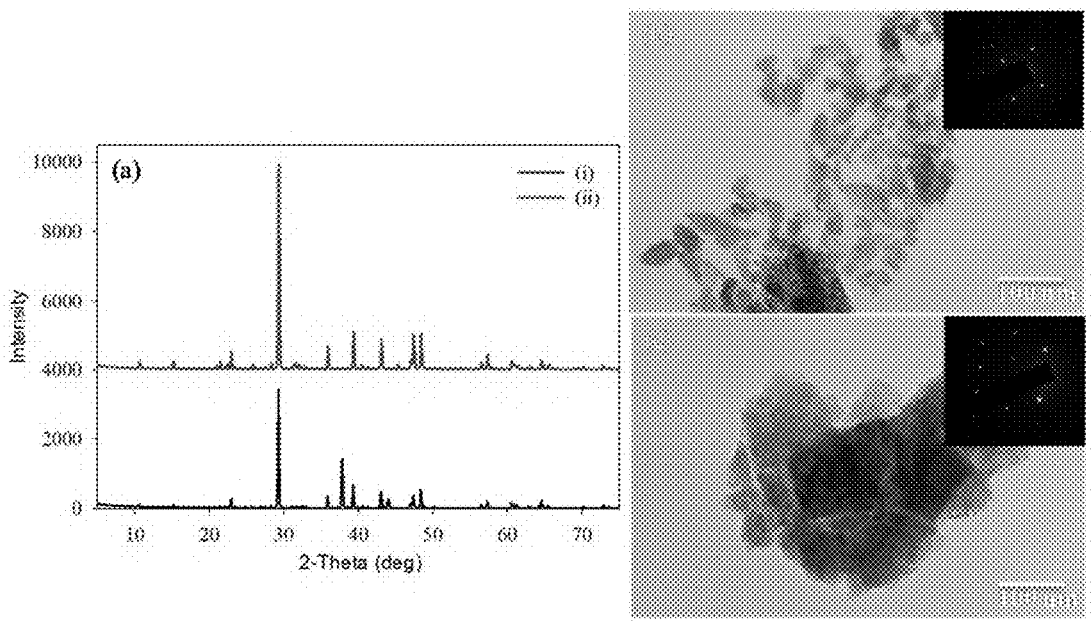

BIO-CONVERSION OF REFINERY WASTE STREAMS

FIELD OF THE INVENTION

The present invention relates to a process of conversion of waste streams of petroleum refinery into industrially useful products.

BACKGROUND OF THE INVENTION

Aqueous alkali metal hydroxide solution is used for removal of various toxicants like sulphides, merceptans, amines, naphthenic acids phenols etc from gaseous and hydrocarbon streams in oil refinery processes. Once these contaminants come in contact and react with caustic solution, it cannot be further utilized and is known as spent caustic. The typical composition of spent caustic may contain about 3-12% of the NaOH along with significant quantities of toxic compounds like sulphides, mercaptans, amines, naphthenic acids, phenols and their derivatives, hydrocarbons and few other inorganic and organic compounds. Owing to presence of these contaminants and high salinity and high pH, spent caustics are most difficult of all industrial wastes to dispose properly. Spent caustic is disposed off by very expensive and environmentally reactive methods such as high dilutions and then treatment at ETP, deep well injections, incineration, wet air oxidation, humid hydrogen peroxide oxidation etc.

In addition to above, waste streams like flue gas containing $CO_2$ and other air pollutants and desalter washing which contains high concentration of salt are also produced in refinery operation which poised negative impact on environment and need to be treated.

US 2004/0040671A1 describes a method in which SC effluent is supplied to a submerged combustion gas evaporator in which hot combustion gas containing $CO_2$ is injected into caustic liquid to concentrate the liquid and convert a hydroxide constituent to a carbonates which is then separated from waste stream.

U.S. Pat. No. 5,244,756 describes a process which introduces refinery gas containing $CO_2$ and hydrogen sulfide into a sodium hydroxide solution to convert the carbon dioxide to sodium carbonates.

U.S. Pat. No. 7,713,399 B2 described a method for treatment of spent caustic where $CO_2$ is used and aqueous sodium sulfate, sodium carbonate and sodium chloride is obtained.

EP2354099 discloses a process for conversion of divalent cations present in waste brine into useful carbonates, using waste gas stream containing $CO_2$ in the presence of halotolerant microorganisms exhibiting carbonic anhydrase activity.

U.S. Pat. Nos. 8,480,796, 8,329,498, 8,329,460, US 20130224842, US20120107899, CA 2813640 A1, WO2008095057A2 disclose the application of carbonic anhydrase for $CO_2$ capture. All methods discussed therein use costly buffers for enzyme activity, which is not required in present invention. Moreover, none of the prior arts have disclosed use of carbonic anhydrase which can work at pH>13 and salinity >4% and also none of the prior arts have used this enzyme for treatment of waste streams like spent caustic along with CO2.

The present invention addresses the above problems which involves the treatment of refinery waste into industrially useful products by an environment friendly method using a carbonic anhydrase enzyme at high pH (>10) and salinity (0.1-10%) and converting waste refinery streams comprising of spent caustic, brine streams and flue gases containing CO2 into useful products such as nano-sized carbonates. The present invention also addresses the problem of disposal of residual liquid phase by treatment with a consortia of specific microbes.

SUMMARY OF THE INVENTION

Accordingly, the main embodiment of the present invention provides a process of converting refinery waste into nano-sized carbonates, said process comprising the steps of:
  (a) mixing the refinery waste in a stirred reactor containing biocatalyst;
  (b) adding brine solution to the mixture of step (a);
  (c) sparging carbon dioxide rich gas to the mixture of step (b); and
  (c) obtaining precipitated nano-sized carbonates.

Yet another embodiment of the present invention provides a process of converting refinery waste streams comprising the steps of:
  (a) mixing the refinery waste stream in a stirred reactor containing biocatalyst;
  (b) adding brine solution to the mixture of step (a);
  (c) sparging carbon dioxide rich gas to the mixture of step (b);
  (d) separating the aqueous/liquid phase to obtain precipitated nano-sized carbonate;
  (e) treating the aqueous/liquid phase with a microbial consortia; and
  (f) obtaining a aqueous phase free of contaminants and biomass of microbial consortia

BRIEF DESCRIPTION OF THE DRAWING

FIG. 1 illustrates an XRD pattern of nano-carbonate particles.

DESCRIPTION OF THE INVENTION

While the invention is susceptible to various modifications and/or alternative processes and/or compositions, specific embodiment thereof has been shown by way of example in the drawings and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The graphs, tables, formulas, protocols have been represented where appropriate by conventional representations in the drawings, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms "comprises", "comprising", or any other variations thereof, are intended to cover a non-exclusive inclusion, such that one or more processes or composition/s or systems or methods proceeded by "comprises . . . a" does not, without more constraints, preclude the existence of other processes, sub-processes, composition, sub-compositions, minor or major compositions or other elements or other structures or additional processes or compositions or additional elements or additional features or additional characteristics or additional attributes.

Definitions

For the purposes of this invention, the following terms will have the meaning as specified therein:

As used herein, the terms "Nano-Sized Carbonates", when used in the context of the present invention refer the carbonates/bicarbonates having particle size less than 200 nm.

As used herein, the terms "Biocatalyst or Biological Catalyst", when used in the context of the present invention refers to carbonic anhydrase catalyst obtained from the microbes as herein described in the present invention. The microbes selected from *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028).

As used herein, the terms "Microbial Consortia or Consortia of specific Microbes", when used in the context of the present invention refers when used in the context of the present invention refers to consortium containing mixture of multiple microorganisms selected from *Pseudomonas putida* (MTCC 5869), *Bacillus substilis* (MTCC 5386), *Pseudomonas aeruginosa* (MTCC 5389), *Peudomonas aerugiosa* (MTCC 5388), *Lysinibacillus* sp. (MTCC 5666) capable of treating or breaking down contaminants from residual liquid phase or aqueous phase obtained after the removal of carbonates containing contaminants to liquid free contaminants.

As used herein, the term "Residual liquid phase or Aqueous Liquid Phase or Aqueous Phase or Liquid Phase", when used in the context of the present invention refers that phase/residue of refinery waste or spent caustic which is obtained after removal or precipitation of carbonates from the refinery waste or spent caustic. This phase comprises of contaminants such as sulphides, phenols, hydrocarbons, naphthenic acid, thiols, mercaptans etc. In other words, in context of the present invention the "Residual liquid phase or Aqueous Liquid Phase or Aqueous Phase or Liquid Phase" is that part of spent caustic or refinery waste from which carbonates or nano-sized carbonates have been removed. However "Residual liquid phase or Aqueous Liquid Phase or Aqueous Phase or Liquid Phase" of the spent caustic still contains contaminants such as sulphides, phenols, hydrocarbons, naphthenic acid, thiols, mercaptans etc., which are removed by the second step as herein described.

As used herein, the term "The Industrially useful Products" when used in the context of the present invention refers to nanosized carbonates/bicarbonates. The nano-particles as herein described in the present invention could be used in other industrial processes such as paper, cement, ink, paint, or coating production plants etc.

As used herein, the term "value added product/s" when used in the context of the present invention refers to nano-sized carbonates/bicarbonates. The nano-particles as herein described in the present invention could be used in industrial processes such as lubricants, paper, cement, ink, paint, or coating production plants etc which make the process economical.

The present invention relates to a process for treatment of refinery waste streams into industrially useful product using a biological catalyst. Further the present invention also relates to a process of conversion of waste refinery streams wherein spent caustic, flue gas containing $CO_2$ and brine are converted into carbonates using carbonic anhydrase tolerant to high pH and salinity. In addition the present invention also relates to a process treatment of residual liquid phase after removal of carbonates with consortia of microbes to obtain the liquid free from contaminants.

The present invention addresses the problem that involves the treatment of refinery wastes into industrially useful products by an environment friendly method using a carbonic anhydrase enzyme which is tolerant to high pH (>10) and salinity (0.1-10%) and capable of converting spent caustic and CO2 in flue gases into useful products such as carbonates.

An aspect of the present invention provides a method for disposal of refinery waste streams. Another aspect of the present invention provides a method for transforming refinery waste streams to value added product using biocatalyst. Yet another aspect of the present invention provides an environmental friendly bio-assisted method for disposal of refinery waste streams and transforming such refinery waste streams to value added product using biological catalysts.

Thus in the present invention, a process is provided for converting refinery waste into nano-sized carbonates wherein spent caustic is kept in a stirred reactor along with biocatalyst carbonic anhydrase enzyme. In one aspect of the present invention carbonic anhydrase enzyme can be used in free form or in the immobilized form. To this, brine solution is passed to maintain the metal ion concentration and an industrial flue gas containing $CO_2$ is sparged, which results precipitation of metal carbonates. The $CO_2$ may be sparged either in macrobubble or microbubble or nanobubble size using suitable sparger or device. To prevent the release of volatile compounds from the system, gaseous phases were continuously recycled. The recycled gas is first passed to a condenser to recover the volatile components and condensate was collected in another reactor.

The aqueous phase decanted from precipitated carbonates and its washing contains the sulphides, phenols, hydrocarbons, naphthenic acid, thiols, mercaptans etc. The aqueous phase retained after carbonate precipitation was introduced in the reactor having collected the volatile compounds. It was treated using specific consortia as described in the present invention.

In the present invention the carbon dioxide can be obtained from various sources like flue gas, bio-gas plant exhaust and combustion exhaust gases, etc. The gas may contain $CO_2$ in the range from 1-25% with other contaminants like $NO_x$ and $SO_x$. The enzyme composition is stable and effective in presence of 99.99% $CO_2$ environment.

In the present invention, the brine solution can be obtained from various sources like crude oil-desalter unit, produced water, reverse osmosis plant reject, cooling tower blow down etc. The brine solution which has total dissolved solids (TDS) in the range of 10 ppm to 100000 ppm can be used in the present invention. The brine may contain various metal chloride, sulphate, phosphate, nitrate etc.

In one aspect the present invention provides a process of transforming refinery waste streams i.e., spent caustic, brine streams and flue gases containing CO2 into useful products wherein the first step comprises of formation of the carbonates or obtaining nano sized carbonates using biocatalyst carbonic anhydrase obtained from microbes as herein described, following this the second step involves breakdown of aqueous phase or the liquid phase using microbial consortia to obtain a liquid phase which is having more than 98% reduction in sulphides, phenols, hydrocarbons, naphthenic acid, thiols or mercaptans, etc.

In other words and more specifically the another aspect of the present invention provides a process of treating spent caustic, brine streams and flue gases containing CO2 into by two-step process, wherein in the first step carbonates or nano-sized carbonates are obtained and thereafter the decanted liquid i.e. the aqueous or liquid phase is further degraded or broken down to obtain a spent caustic which is having 98% reduction in sulphides, phenols, hydrocarbons, naphthenic acid, thiols or mercaptans, etc.

In another aspect the present invention provides a process of treating refinery waste stream containing spent caustic, flue gas and brine solution by a two-step process described above wherein the first step and the second step as described above and elsewhere in the description including examples may be carried out in batch, semi-continuous or continuous process.

In another aspect the present invention provides a process of treating refinery waste stream containing spent caustic, flue gas and brine solution by a two-step process described above wherein the first step and the seconds step as described above and elsewhere in the description including examples is preferably carried out as continuous process. When the process done in continuous mode, the treatment time in the second stage i.e., treatment of the aqueous mode the treatment time is 1-4 days.

Production of the Biocatalyst:

The biocatalyst which can be used in the present invention is carbonic anhydrase which can tolerate high pH (>10), tolerate high salinity (0.1-10%) and high temperature (>80° C.). This biocatalyst improves the solubility of $CO_2$ into aqueous phase. The biocatalyst can be obtained from wild or genetically modified bacteria, fungi, algae and from other biological sources. Some of the example of the microbes from which anhydrase enzyme can be obtained includes *Enterobacter aerogenes* (MTCC 25016), *Lysinibacillus* sp. (MTCC 25029), *Bacillus thermoleovorans* (MTCC 25023), *Bacillus stearothermophilus* (MTCC 25030), *Arthrobacter* sp. (MTCC 25028) or from their mutants/derivatives. The source of the microbes is soil collected from the Indian Oil Corporation Limited Panipat Refinery in Panipat, Haryana, India. The geographical origin of the microbes is Indian Oil Corporation Limited R&D Centre in Faridabad, Haryana, India. The foresaid microbes have been deposited with the Microbial Type Culture Collection (MTCC), Chandigarh as required under the Budapest Treaty. The MTCC assigned their respective Accession numbers as recited above.

For the production of the carbonic anhydrase the bacteria or their combination can be grown in media containing $Na_2CO_3$ (1-5 g/l), $NaHCO_3$ (0.5-2.5 g/l) $KH_2PO_4$ (0.5-4 g/l), $K_2HPO_4$ (0.5-4 g/l), $MgSO_4$ (0.1-1.0 g/l), $(NH4)_2SO_4$ (0.25-0.50 g/l), $KNO_3$ (0.15-4.75 g/l), $ZnSO4$ (0.2-20 g/l), $NaCl$ (0.2-10 g/l), yeast extract (0.1-4 g/l), nitrogen source (0.2-50 g/l), carbon source (0.2-50 g/l), Trace element (2 ml to 15 ml of solution). The trace element solution comprises of Nitrilotriacetic acid (0.1-1.0 g/l), $FeSO_4.7H_2O$ (0.01-0.15 g/l), $MnCl_2.4H_2O$ (0.001-0.005 g/l), $CoCl_2.6H_2O$ (0.005-0.02 g/l), $CaCl_2.2H_2O$ (0.01-0.5 g/l), $ZnCl_2$ (0.01-0.15 g/l), $CuCl_2.H_2O$ (0.01-0.03 g/l), $H_3BO_3$ (0.002-0.02 g/l), $Na_2MoO_4$ (0.001-0.02 g/l), $Na_2SeO_3$ (0.005-0.02 g/l), $NiSO_4$ (0.01-0.03 g/l), $SnCl_2$ (0.01-0.03 g/l). The carbon sources can be used may include inorganic carbon source like sucrose, glucose, acetate, plant biomass hydrolysate, organic material, glycerol and inorganic carbon source like carbon dioxide, inorganic carbonates/bicarbonates. The nitrogen sources may include ammonium chloride, potassium nitrate, urea, corn steep liquor based.

In order to produce the carbonic anhydrase enzyme, the microbe can be inoculated in the above media in anaerobic or aerobic or micro-aerophilic conditions using the techniques known in the art and can be incubated at a temperature ranging from 20-65° C. The pH of the media used for production of the enzyme may be in range of 6-12 with or without shaking/stirring. For the enzyme production, the microbes are required to be incubated for 10-48 hrs. Subsequently, the intracellular and/or extracellular carbonic anhydrase enzyme can be purified by method known the art with respect to purification of proteins like ammonium sulfate precipitation, molecular filtration and agarose bound p-aminomethylbenzenesulfonamide (p-AMBS-agarose) column chromatography. The purified enzyme is then characterized with respect to molecular weight, enzyme activity, pH stability, salinity tolerance and thermostability.

The biocatalyst may also be used in either immobilized or free forms. The immobilization agents includes carbon nanotubes, metal organic framework, zeolites, Zinc-ferrite, nickel ferrite, Zinc-nickel (Zn—Ni) ferrite, polyurethane, glass beads or any other suitable matrixes.

Conversion of the Refinery Waste Streams to Value Added Product

The refinery spent caustic and brine solution obtained from crude desalting process were mixed in a stirred reactor along with biocatalyst. The ratio of the refinery spent caustic and brine solution may be in the range of 1:1 to 1:0.10. The enzyme loading may vary from 2-20 units/ml of the reaction mixture. The stirring is done by any suitable device in the range from 20-200 rpm. To this, industrial flue gas is sparged (0.1-20 L/min) for 0.5-30 minutes at temperature ranging from 25-85° C. To prevent the release of volatile compounds from the system, gas phases were continuously recycled. The recycled gas first passed to a condenser (maintained at 1-5° C.) to recover the volatile compounds and condensate was collected in another reactor. This results in precipitation of metal carbonates. A control without biocatalyst was also kept under same experimental conditions. The precipitate obtained is separated and washed. It is analysed for its composition by XRF, XRD and TEM (FIG. 1). The aqueous phase decanted from precipitated carbonates, wherein the aqueous phase contains sulphides, phenols, hydrocarbons, etc.

The TEM analysis shows that nano particle of $CaCO_3$ was found with size from 60 to 150 nm in presence of enzyme as shown in FIG. 1 (section (a)) while without enzyme the size was not irregular in shape with a size around 500 nm as shown in FIG. 1 (section (b)). This shows that enzyme can be used for converting $CO_2$ to nano sized $CaCO_3$ which have several industrial applications such as these nanoparticles could be used in other industrial processes such as paper, cement, ink, paint, or coating production plants etc which make the process economically desirable, and even profitable.

Treatment of the Aqueous Phase

The aqueous phase that is obtained after carbonate precipitation is then introduced in the reactor having collected the volatile compounds. It was treated using a microbial consortia developed in the present invention. The consortia is developed and used as per method described herein. A microbial consortium consisting of *Pseudomonas putida* (MTCC 5869), *Bacillus substilis* (MTCC 5386), *Pseudomonas aeruginosa* (MTCC 5389), *Peudomonas aerugiosa* (MTCC 5388), *Lysinibacillus* sp. (MTCC 5666) were prepared and evaluated CSTR with air bubbling system. Treatment is done in batch mode. The source of the microbes is soil collected from the Indian Oil Corporation Limited Panipat Refinery in Panipat, Haryana, India. The geographical origin of the microbes is Indian Oil Corporation Limited Panipat Refinery in Panipat, Haryana, India. The foresaid microbes have been deposited with the Microbial Type Culture Collection (MTCC), Chandigarh as required under the Budapest Treaty. The MTCC assigned their respective Accession numbers as recited above.

The aqueous liquid after carbonate precipitation was fed in the reactor. Along with nutrient system comprising of $K_2HPO_4$ (0.5-10 g/l), $KH_2PO_4$ (1-4 g/l), $MgCl_2$ (0.2-2.0 g/l), urea (1-2 g/l) yeast extract (2-15 g/l) sodium nitrate (4 g/l). The aqueous phase was used as such without amending the pH. The temperature of the reactor maintained in range from 20-60° C. The percentage of oxygen saturation was controlled in the range of 50 to 100%. The stirring was done at 200-600 rpm. To prevent the release of volatile compounds from the system, gas phases were continuously recycled. The recycled gas first passed to a condenser (maintained at 1-5° C.) to recover the volatile compounds and metabolites. An abiotic control with similar conditions was also operated. At the time interval samples were taken and were analyzed for CFU/ml (Colony Forming Unit/ml) on agar plate as well for determining the concentration of contaminant by suitable analytical techniques. In batch mode, after 24 hours, the treated spent caustic is reduced by more than 98% in total sulfur, sulphides, mercaptans, hydrocarbon, phenol and other contaminants in comparison to abiotic control without the microbial consortia. Once, the contaminant reduced to substantial level (i.e. more than 98%), the treated spent caustic is removed and biomass of microbial consortia is recovered. The recovered biomass of microbial consortia can be recycled and used for treatment fresh aqueous layer of spent caustic after sparging $CO_2$ in presence of carbonic anhydrase.

In another aspect of the present invention, the microbial consortium was prepared to take the benefits of the synergy of microbes' metabolic activity. The efficiency of the microbial consortium to degrade contaminants of aqueous media was evaluated in shake flask at 35° C. and 120 rpm. The samples were taken at regular time interval and were analyzed for CFU/ml on agar plate as well for concentration of contaminant by suitable analytical techniques. The microbial consortia were found to have higher growth and degradation ability were selected. In another aspect of the present invention microbial consortium may be used in free form or immobilized form.

Accordingly the main embodiment of the present invention provides a process of converting refinery waste streams selected from spent caustic, brine and flue gases containing $CO_2$ into nano-sized carbonates, comprising the steps of:
(a) mixing the refinery waste stream in a stirred reactor containing biocatalyst mixing the spent caustic in a stirred reactor containing biocatalyst, wherein the biocatalyst is obtained from microbe selected from *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028);
(b) adding brine solution to the mixture of step (a);
(c) sparging carbon dioxide rich gas to the mixture of step (b);
(d) separating the aqueous/liquid phase to obtain precipitated nano-sized carbonate;
(e) treating the aqueous/liquid phase with a microbial consortia is selected from a mixture of any one of *Pseudomonas putida* (MTCC 5869), *Bacillus substilis* (MTCC 5386), *Pseudomonas aeruginosa* (MTCC 5389), *Peudomonas aerugiosa* (MTCC 5388) and *Lysinibacillus* sp. (MTCC 5666); and
(f) obtaining a spent caustic free of contaminants Another embodiment of the present invention provides a wherein the refinery waste stream is spent caustic.

Another embodiment of the present invention provides a wherein the biocatalyst is carbonic anhydrase having a concentration in range of 2-20 units/ml of the reaction mixture and is capable of withstanding pH above 10, salinity in the range of 0.1-10% and temperature above 80° C.

Another embodiment of the present invention provides a wherein the source of carbon dioxide gas is selected from flue gas or bio-gas plant exhaust.

Another embodiment of the present invention provides a wherein the brine solution is obtained from sources selected from crude oil-desalter unit, produced water, reverse osmosis plant reject or cooling tower blow down.

Another embodiment of the present invention provides a wherein the ratio of refinery spent caustic and brine solution is in the range of 1:1 to 1:0.10.

Another embodiment of the present invention provides a wherein the process as herein described are carried out at a temperature in the range of 25-85° C. for 0.5-30 minutes.

Another embodiment of the present invention provides a wherein the biocatalyst may be immobilized in the immobilization agents selected from carbon nanotubes, metal organic framework, zeolites, Zinc-ferrite, nickel ferrite, Zinc-nickel (Zn—Ni) ferrite, polyurethane, glass beads or any other suitable matrixes.

Another embodiment of the present invention provides a wherein process of treating the aqueous/liquid phase with a microbial consortia as herein described is carried out at a temperature in the range of 20-60° C. and stirring of the reaction is carried in range of 200-600 rpm.

Yet another embodiment of the present invention provides a process of converting refinery waste into nano-sized carbonates, said process comprising the steps of:
(a) mixing the refinery waste in a stirred reactor containing biocatalyst, wherein the biocatalyst is obtained from microbes selected from *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028);
(b) adding brine solution to the mixture of step (a);
(c) sparging carbon dioxide rich gas to the mixture of step (b); and
(d) obtaining precipitated nano-sized carbonates.

Yet another embodiment of the present invention provides a process as herein described wherein the refinery waste is spent caustic.

Yet another embodiment of the present invention provides a process as herein described wherein the biocatalyst is carbonic anhydrase having a concentration in range of 2-20 units/ml of the reaction mixture and is capable of withstanding pH above 10, salinity in the range of 0.1-10% and temperature above 80° C.

Yet another embodiment of the present invention provides a process as herein described wherein the source of carbon dioxide gas is selected from flue gas or bio-gas plant exhaust.

Yet another embodiment of the present invention provides a process as herein described wherein the brine solution is obtained from sources selected from crude oil-desalter unit, produced water, reverse osmosis plant reject or cooling tower blow down.

Yet another embodiment of the present invention provides a process as herein described wherein the ratio of refinery spent caustic and brine solution is in the range of 1:1 to 1:0.10.

Yet another embodiment of the present invention provides a process as herein described wherein the process is carried out at a temperature in the range of 25-85° C. for 0.5-30 minutes.

Yet another embodiment of the present invention provides a process as herein described wherein the biocatalyst may be immobilized in the immobilization agents selected from carbon nanotubes, metal organic framework, zeolites, Zinc-ferrite, nickel ferrite, Zinc-nickel (Zn—Ni) ferrite, polyurethane, glass beads or any other suitable matrixes.

Yet another embodiment of the present invention provides a process as herein described wherein the biocatalyst may be immobilized in the immobilization agents selected from carbon nanotubes, metal organic framework, zeolites, Zinc-ferrite, nickel ferrite, Zinc-nickel (Zn—Ni) ferrite, polyurethane or glass beads.

Yet another embodiment of the present invention provides a process as herein described wherein the total dissolved solids in brine solution in the range of 10 ppm to 100000 ppm.

Yet another embodiment of the present invention provides a process as herein described wherein the nano-sized carbonate has a particle size in the range of 50-100 nm.

Another embodiment of the present invention provides process of treating aqueous or liquid phase comprising the steps of:
  (a) obtaining the aqueous/liquid phase to from the precipitated nano-sized carbonate;
  (b) treating the aqueous/liquid phase with a microbial consortia is selected from a mixture of *Pseudomonas putida* (MTCC 5869), *Bacillus substilis* (MTCC 5386), *Pseudomonas aeruginosa* (MTCC 5389), *Peudomonas aerugiosa* (MTCC 5388) and *Lysinibacillus* sp. (MTCC 5666); and
  (c) obtaining a lipid free of contaminants and normal salinity.

Another embodiment of the present invention provides a process of treating aqueous/liquid phase as herein described wherein the contaminants of aqueous/liquid phase comprises of sulphides, phenols, hydrocarbons, naphthenic acid, thiols or mercaptans, etc.

Another embodiment of the present invention provides a process of treating aqueous/liquid phase as herein described wherein the contaminants of aqueous/liquid phase are selected from sulphides, phenols, hydrocarbons, naphthenic acid, thiols and mercaptans.

Another embodiment of the present invention provides a process of treating aqueous/liquid phase as herein described wherein the contaminants of aqueous/liquid phase are selected from sulphides, phenols, hydrocarbons and mercaptans.

Another embodiment of the present invention provides a process of treating aqueous/liquid phase or the aqueous/liquid phase spent caustic, wherein the treated aqueous/liquid phase or the aqueous/liquid phase spent caustic has more than 98% reduction in sulphides, phenols, hydrocarbons, naphthenic acid, thiols, mercaptans or other contaminants.

Another embodiment of the present invention provides a process of treating aqueous/liquid phase which comprises of spent caustic, wherein the treated spent caustic has more than 98% reduction in sulphides, phenols, hydrocarbons, naphthenic acid, thiols, mercaptans or other contaminants.

Another embodiment of the present invention provides a process of treating aqueous/liquid phase, wherein the treated aqueous/liquid phase has more than 98% reduction in sulphides, phenols, hydrocarbons, naphthenic acid, thiols, mercaptans or other contaminants.

Yet another embodiment of the present invention provides a wherein the microbial consortia is selected from a mixture of *Pseudomonas putida* (MTCC 5869), *Bacillus substilis* (MTCC 5386), *Pseudomonas aeruginosa* (MTCC 5389), *Peudomonas aerugiosa* (MTCC 5388) and *Lysinibacillus* sp. (MTCC 5666).

Yet another embodiment of the present invention provides a wherein the microbial consortia is selected from a mixture of *Pseudomonas putida* (MTCC 5869), *Bacillus substilis* (MTCC 5386), *Pseudomonas aeruginosa* (MTCC 5389), *Peudomonas aerugiosa* (MTCC 5388) or *Lysinibacillus* sp. (MTCC 5666).

Yet another embodiment of the present invention provides a wherein the total dissolved solids in brine solution in the range of 10 ppm to 100000 ppm.

Yet another embodiment of the present invention provides a wherein the nano-sized carbonate have a particle size in the range of 50-100 nm.

Yet another embodiment of the present invention provides a wherein the microbial consortia is selected from a mixture of *Pseudomonas putida* (MTCC 5869), *Bacillus substilis* (MTCC 5386), *Pseudomonas aeruginosa* (MTCC 5389), *Peudomonas aerugiosa* (MTCC 5388) and *Lysinibacillus* sp. (MTCC 5666) for treatment of aqueous or liquid phase.

Yet another embodiment of the present invention provides a wherein the microbial consortia is selected from a mixture of anyone of *Pseudomonas putida* (MTCC 5869), *Bacillus substilis* (MTCC 5386), *Pseudomonas aeruginosa* (MTCC 5389) or *Peudomonas aerugiosa* (MTCC 5388), *Lysinibacillus* sp. (MTCC 5666) for treatment of aqueous or liquid phase.

Yet another embodiment of the present invention provides a wherein the microbial consortia is selected from a mixture of any two of *Pseudomonas putida* (MTCC 5869), *Bacillus substilis* (MTCC 5386), *Pseudomonas aeruginosa* (MTCC 5389) or *Peudomonas aerugiosa* (MTCC 5388), *Lysinibacillus* sp. (MTCC 5666) for treatment of aqueous or liquid phase.

Yet another embodiment of the present invention provides a wherein the microbial consortia is selected from a mixture of any three of *Pseudomonas putida* (MTCC 5869), *Bacillus substilis* (MTCC 5386), *Pseudomonas aeruginosa* (MTCC 5389) or *Peudomonas aerugiosa* (MTCC 5388), *Lysinibacillus* sp. (MTCC 5666) for treatment of aqueous or liquid phase.

Yet another embodiment of the present invention provides a wherein the microbial consortia is selected from a mixture of any four of *Pseudomonas putida* (MTCC 5869), *Bacillus substilis* (MTCC 5386), *Pseudomonas aeruginosa* (MTCC 5389) or *Peudomonas aerugiosa* (MTCC 5388), *Lysinibacillus* sp. (MTCC 5666) for treatment of aqueous or liquid phase.

Yet another embodiment of the present invention provides a wherein the microbial consortia is selected from a mixture of any five of *Pseudomonas putida* (MTCC 5869), *Bacillus substilis* (MTCC 5386), *Pseudomonas aeruginosa* (MTCC 5389) or *Peudomonas aerugiosa* (MTCC 5388), *Lysinibacillus* sp. (MTCC 5666) for treatment of aqueous or liquid phase.

Yet another embodiment of the present invention provides a wherein the microbial consortia is selected from a mixture of all five of *Pseudomonas putida* (MTCC 5869), *Bacillus substilis* (MTCC 5386), *Pseudomonas aeruginosa* (MTCC 5389) and *Peudomonas aerugiosa* (MTCC 5388), *Lysinibacillus* sp. (MTCC 5666) for treatment of aqueous or liquid phase.

Yet another embodiment of the present invention provides a wherein the microbial consortia consist mixture of *Pseudomonas putida* (MTCC 5869), *Bacillus substilis* (MTCC 5386), *Pseudomonas aeruginosa* (MTCC 5389) and *Peudomonas aerugiosa* (MTCC 5388), *Lysinibacillus* sp. (MTCC 5666) for treatment of aqueous or liquid phase.

Yet another embodiment of the present invention provides a wherein the microbial consortia is selected from a mixture of any one of *Enterobacter aerogenes* (MTCC 25016), *Lysinibacillus* sp. (MTCC 25029), *Bacillus thermoleovorans* (MTCC 25023) or *Bacillus stearothermophilus* (MTCC 25030) or *Arthrobacter* sp. (MTCC 25028) for the production of carbonic anhydrase.

Yet another embodiment of the present invention provides a wherein the microbial consortia is selected from a mixture of any two of *Enterobacter aerogenes* (MTCC 25016), *Lysinibacillus* sp. (MTCC 25029), *Bacillus thermoleovorans* (MTCC 25023) or *Bacillus stearothermophilus* (MTCC 25030) or *Arthrobacter* sp. (MTCC 25028) for the production of carbonic anhydrase. Yet another embodiment of the present invention provides a wherein the microbial consortia is selected from a mixture of any three of *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028) for the production of carbonic anhydrase.

Yet another embodiment of the present invention provides a wherein the microbial consortia is selected from a mixture of any four of *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028) for the production of carbonic anhydrase.

Yet another embodiment of the present invention provides a microbe selected from any five of *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028) for the production of carbonic anhydrase.

Yet another embodiment of the present invention provides a microbe selected from all five *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) and *Arthrobacter* sp. (MTCC 25028) for the production of carbonic anhydrase.

Yet another embodiment of the present invention provides consortia of microbe consisting of *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) and *Arthrobacter* sp. (MTCC 25028) for the production of carbonic anhydrase.

The present invention provides various microbes that can be used for the purpose of production of biocatalyst carbonic anhydrase as herein described. The various embodiments of the present invention provides the alternate means by which the microbes may be used alone or in combination (of two, three, four or five) for the production of biocatalyst carbonic anhydrase.

Another embodiment of the present invention provides a process as herein described wherein the ratio of refinery spent caustic and brine solution is 1:1 or 10:1.

Another embodiment of the present invention provides a process as herein described wherein the ratio of refinery spent caustic and brine solution is 1:0.10.

Another embodiment of the present invention provides a process as herein described wherein the process is carried out at a temperature in the range of 85° C. for 0.5-30 minutes.

Another embodiment of the present invention provides a process as herein described wherein the process is carried out at a temperature in the range of 80° C. for 0.5-30 minutes.

Another embodiment of the present invention provides a process as herein described wherein the process is carried out at a temperature in the range of 25° C. for 0.5-30 minutes.

Another embodiment of the present invention provides a process as herein described wherein the nano-sized carbonate has a particle size of 50 nm.

Another embodiment of the present invention provides a process as herein described wherein the nano-sized carbonate has a particle size in the range of 100 nm.

Another embodiment of the present invention provides a process as herein described wherein the nano-sized carbonate has a particle size in the range of 60-150 nm.

Another embodiment of the present invention provides a process as herein described wherein the nano-sized carbonate has a particle size in the range of 50-200 nm.

Another embodiment of the present invention provides a process as herein described wherein the nano-sized carbonate has a particle size of 60 nm.

Another embodiment of the present invention provides a process as herein described wherein the nano-sized carbonate has a particle size of 150 nm.

Yet another embodiment of the present invention provides a wherein process of treating the aqueous/liquid phase with a microbial consortia as herein described is carried out at a temperature of 20° C. and stirring of the reaction is carried in range of 200-600 rpm.

Yet another embodiment of the present invention provides a wherein process of treating the aqueous/liquid phase with a microbial consortia as herein described is carried out at a temperature of 60° C. and stirring of the reaction is carried in range of 200-600 rpm.

Another aspect the present invention provides a microbe as herein described wherein the any one of the microbe alone or in combination of two, three, four or five microbes can be used for the production of carbonic anhydrase.

Another embodiment of the present invention provides a process as herein described wherein the biocatalyst is carbonic anhydrase having a concentration in range of 2-20 units/ml of the reaction mixture and is capable of withstanding pH above 13, salinity in the range of 0.1-10% and temperature above 80° C.

Another embodiment of the present invention provides a process as herein described wherein the biocatalyst is carbonic anhydrase having a concentration in range of 2-20 units/ml of the reaction mixture and is capable of withstanding pH up to 13, salinity in the range of 0.1-10% and temperature above 80° C.

Another embodiment of the present invention provides a process as herein described wherein the biocatalyst is carbonic anhydrase having a concentration in range of 2-20 units/ml of the reaction mixture and is capable of withstanding pH up to 13, salinity of 10% and temperature above 80° C.

Another embodiment of the present invention provides a process as herein described wherein the biocatalyst is carbonic anhydrase having a concentration in range of 2-20 units/ml of the reaction mixture and is capable of withstanding pH up to 13, salinity of 10% and temperature of 80° C.

Another embodiment of the present invention provides a process as herein described wherein the biocatalyst is carbonic anhydrase having a concentration in range of 2-20 units/ml of the reaction mixture and is capable of withstanding pH up to 13, salinity of 10% and temperature of 85° C.

Another embodiment of the present invention provides a process as herein described wherein the biocatalyst is carbonic anhydrase having a concentration in range of 2-20 units/ml of the reaction mixture and is capable of withstanding pH of 13, salinity of 10% and temperature of 85° C.

Another embodiment of the present invention provides a process as herein described wherein the biocatalyst is carbonic anhydrase having a concentration in range of 20 units/ml of the reaction mixture and is capable of withstanding pH of 13, salinity of 10% and temperature of 85° C.

Another embodiment of the present invention provides a process as herein described wherein the biocatalyst is carbonic anhydrase having a concentration in range of 2 units/ml of the reaction mixture and is capable of withstanding pH of 13, salinity of 10% and temperature of 85° C.

Another embodiment of the present invention provides a process as herein described wherein the biocatalyst is carbonic anhydrase having a concentration in range of 1.75 units/ml of the reaction mixture and is capable of withstanding pH of 13, salinity of 10% and temperature of 85° C.

Another embodiment of the present invention provides a process as herein described wherein the biocatalyst is carbonic anhydrase having a concentration in range of 1.75-20 units/ml of the reaction mixture and is capable of withstanding pH of up to 13, salinity of more than 10% and temperature more than 85° C.

Another embodiment of the present invention provides a process as herein described wherein the biocatalyst is carbonic anhydrase having a concentration in range of 1.75-20 units/ml of the reaction mixture and is capable of withstanding pH of more than 10, salinity of more than 10% and temperature more than 85° C.

Another embodiment of the present invention provides a process as herein described wherein the biocatalyst is carbonic anhydrase having a concentration in range of 2 units/ml of the reaction mixture and is capable of withstanding pH above 10, salinity in the range of 0.1-10% and temperature of 80° C.

Another embodiment of the present invention provides a process as herein described wherein the biocatalyst is carbonic anhydrase having a concentration in range of 20 units/ml of the reaction mixture and is capable of withstanding pH above 10, salinity in the range of 0.1-10% and temperature of 80° C.

Another embodiment of the present invention provides a process as herein described wherein the biocatalyst is carbonic anhydrase having a concentration in range of 2 units/ml of the reaction mixture and is capable of withstanding pH 10, salinity of 10% and temperature of 80° C.

Another embodiment of the present invention provides a process as herein described wherein the biocatalyst is carbonic anhydrase having a concentration in range of 20 units/ml of the reaction mixture and is capable of withstanding pH 10, salinity of 10% and temperature of 80° C.

Another embodiment of the present invention provides a process as herein described wherein the biocatalyst is carbonic anhydrase having a concentration in range of 20 units/ml of the reaction mixture and is capable of withstanding pH 10, salinity of 10% and temperature of 85° C.

Another embodiment of the present invention provides a process as herein described wherein the biocatalyst is carbonic anhydrase having a concentration in range of 2 units/ml of the reaction mixture and is capable of withstanding pH 10, salinity of 10% and temperature of 85° C.

Another aspect the present invention provides a microbe as herein described wherein the any one of the microbe alone or in combination of two, three, four or five microbes can be used in form of a microbial consortia or alone for the treatment of the aqueous or liquid phase.

In another aspect of the present invention the process disclosed for conversion of refinery waste streams into industrially useful products and treatment of residual liquid may be batch, semi continuous or continuous process. While running in the continuous mode the retention Time is 1-4 days.

The present invention provides a method where the brine is treated for its salinity, flue gas for its CO2 content and spent caustic for its contaminants.

Yet another embodiment of the present invention provides for a process of converting refinery waste streams selected from spent caustic, brine and flue gases containing $CO_2$ into nano-sized carbonates, comprising the steps of:
(a) mixing the spent caustic in a stirred reactor containing biocatalyst, wherein the biocatalyst is obtained from microbe selected from anyone of *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028);
(b) adding brine solution to the mixture of step (a);
(c) sparging carbon dioxide rich gas to the mixture of step (b);
(d) separating the aqueous/liquid phase to obtain precipitated nano-sized carbonate;
(e) treating the aqueous/liquid phase with a microbial consortia is selected from a mixture of any one of *Pseudomonas putida* (MTCC 5869), *Bacillus substilis* (MTCC 5386), *Pseudomonas aeruginosa* (MTCC 5389), *Peudomonas aerugiosa* (MTCC 5388) and *Lysinibacillus* sp. (MTCC 5666); and
(f) obtaining a aqueous phase free of contaminants.

Yet another embodiment of the present invention provides for a process of converting refinery waste streams selected from spent caustic, brine and flue gases containing $CO_2$ into nano-sized carbonates, comprising the steps of:
(a) mixing the spent caustic in a stirred reactor containing biocatalyst, wherein the biocatalyst is obtained from microbe selected from anyone of *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028);
(b) adding brine solution to the mixture of step (a);
(c) sparging carbon dioxide rich gas to the mixture of step (b);
(d) separating the aqueous/liquid phase to obtain precipitated nano-sized carbonate;
(e) treating the aqueous/liquid phase with a microbial consortia is a mixture of two or more microbes selected from *Pseudomonas putida* (MTCC 5869), *Bacillus substilis* (MTCC 5386), *Pseudomonas aeruginosa*

(MTCC 5389), *Peudomonas aerugiosa* (MTCC 5388) or *Lysinibacillus* sp. (MTCC 5666); and (f) obtaining a aqueous phase free of contaminants.

Yet another embodiment of the present invention provides for a process of converting refinery waste streams selected from spent caustic, brine and flue gases containing $CO_2$ into nano-sized carbonates, comprising the steps of:
- (a) mixing the spent caustic in a stirred reactor containing biocatalyst, wherein the biocatalyst is obtained from microbe selected from anyone of *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028);
- (b) adding brine solution to the mixture of step (a);
- (c) sparging carbon dioxide rich gas to the mixture of step (b);
- (d) separating the aqueous/liquid phase to obtain precipitated nano-sized carbonate;
- (e) treating the aqueous/liquid phase with a microbial consortia is a mixture of any two or more microbes selected from *Pseudomonas putida* (MTCC 5869), *Bacillus substilis* (MTCC 5386), *Pseudomonas aeruginosa* (MTCC 5389), *Peudomonas aerugiosa* (MTCC 5388) and *Lysinibacillus* sp. (MTCC 5666); and
- (f) obtaining a aqueous phase free of contaminants.

Yet another embodiment of the present invention provides for a process of converting refinery waste streams selected from spent caustic, brine and flue gases containing $CO_2$ into nano-sized carbonates, comprising the steps of:
- (a) mixing the spent caustic in a stirred reactor containing biocatalyst, wherein the biocatalyst is obtained from microbe selected from anyone of *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028);
- (b) adding brine solution to the mixture of step (a);
- (c) sparging carbon dioxide rich gas to the mixture of step (b);
- (d) separating the aqueous/liquid phase to obtain precipitated nano-sized carbonate;
- (e) treating the aqueous/liquid phase with a microbial consortia is a mixture of any three or more microbes selected from *Pseudomonas putida* (MTCC 5869), *Bacillus substilis* (MTCC 5386), *Pseudomonas aeruginosa* (MTCC 5389), *Peudomonas aerugiosa* (MTCC 5388) and *Lysinibacillus* sp. (MTCC 5666); and
- (f) obtaining a aqueous phase free of contaminants.

Yet another embodiment of the present invention provides for a process of converting refinery waste streams selected from spent caustic, brine and flue gases containing $CO_2$ into nano-sized carbonates, comprising the steps of:
- (a) mixing the spent caustic in a stirred reactor containing biocatalyst, wherein the biocatalyst is obtained from microbe selected from anyone of *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028);
- (b) adding brine solution to the mixture of step (a);
- (c) sparging carbon dioxide rich gas to the mixture of step (b);
- (d) separating the aqueous/liquid phase to obtain precipitated nano-sized carbonate;
- (e) treating the aqueous/liquid phase with a microbial consortia is a mixture of any four or more microbes selected from *Pseudomonas putida* (MTCC 5869), *Bacillus substilis* (MTCC 5386), *Pseudomonas aerugiosa* (MTCC 5389), *Peudomonas aerugiosa* (MTCC 5388) and *Lysinibacillus* sp. (MTCC 5666); and
- (f) obtaining a aqueous phase free of contaminants.

Yet another embodiment of the present invention provides for a process of converting refinery waste streams selected from spent caustic, brine and flue gases containing $CO_2$ into nano-sized carbonates, comprising the steps of:
- (a) mixing the spent caustic in a stirred reactor containing biocatalyst, wherein the biocatalyst is obtained from microbe selected from anyone of *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028);
- (b) adding brine solution to the mixture of step (a);
- (c) sparging carbon dioxide rich gas to the mixture of step (b);
- (d) separating the aqueous/liquid phase to obtain precipitated nano-sized carbonate;
- (e) treating the aqueous/liquid phase with a microbial consortia is a mixture of microbes selected from *Pseudomonas putida* (MTCC 5869), *Bacillus substilis* (MTCC 5386), *Pseudomonas aeruginosa* (MTCC 5389), *Peudomonas aerugiosa* (MTCC 5388) and *Lysinibacillus* sp. (MTCC 5666); and
- (f) obtaining a aqueous phase free of contaminants.

The invention will now be explained with the help of following examples. However, the scope of the invention should not be limited to these examples as the person skilled in the art can easily vary the proportion of the ingredients and combinations.

EXAMPLES

Example 1: Preparation of Biocatalyst

The bacterium *Bacillus thermoleovorans* (MTCC 25023) was inoculated in the media containing $Na_2CO_3$ (5), $NaHCO_3$ (2.5 g/l) $KH_2PO_4$ (2 g/l), $K_2HPO_4$ (2.5 g/l), $MgSO_4$ (0.1 g/l), $(NH4)_2SO_4$ (0.25 g/l), $KNO_3$ (2 g/l), $ZnSO4$ (3 g/l), NaCl (10 g/l), yeast extract (2 g/l), urea (3 g/l), glycerol (5 g/l), Trace element (2 ml). The trace element solution comprises Nitrilotriacetic acid (1.0 g/l), $FeSO_4.7H_2O$ (0.15 g/l), $MnCl_2.4H_2O$ (0.005 g/l), $CoCl_2.6H_2O$ (0.02 g/l), $CaCl_2.2H_2O$ (0.5 g/l), $ZnCl_2$ (0.15 g/l), $CuCl_2.H_2O$ (0.03 g/l), $H_3BO_3$ (0.02 g/l), $Na_2MoO_4$ (0.02 g/l), $Na_2SeO_3$ (0.02 g/l), $NiSO_4$ (0.03 g/l), $SnCl_2$ (0.03 g/l).

In order to produce carbonic anhydrase enzyme, the microbe is inoculated in the above media in aerobic conditions and incubated at 40° C. temperature at a pH 8 followed by shaking. The bacterium is incubated for 48 hrs. Subsequently, the extracellular and/or extracelluar carbonic anhydrase enzyme is purified by ammonium sulfate precipitation, molecular filtration and agarose bound p-aminomethylbenzenesulfonamide (p-AMBS-agarose) column chromatography. The purified enzyme was having Molecular weight of 30 KDa characterized with 3500 units/mg activity. The biocatalyst may be used in free form or immobilized form. The enzyme preparation had tolerance up to pH 13, could tolerate salinity of 10% and high temperature of about 80° C.

Conversion of the Refinery Waste Streams to Value Added Product

The 1 L refinery spent caustic (composition given in Table 1) and 1 L brine solution obtained from crude desalting process (composition given in Table 2) were mixed in a stirred reactor along with biocatalyst (1750 units). To this, industrial flue gas was sparged (2 L/min) for 5 minutes at ambient temperature (25° C.). To prevent the release of volatile compounds from the system, gas phases were continuously recycled. The recycled gas first passed to a condenser (maintained at 5° C.) to recover the volatile compounds and condensate was collected in another reactor. This results in precipitation of metal carbonates. A control without biocatalyst and commercially available biocatalyst i.e., carbonic anhydrase from bovine serum (Purchased from Sigma) and human carbonic anhydrase-II (purchased from Sigma) was also kept under same experimental conditions.

The precipitate obtained was separated and washed. It was analysed for its composition by XRF, XRD and TEM. XRF and XRD analysis showed formation of carbonates. In the presence of biocatalyst developed in the invention, higher amount of carbonates was obtained (>5 times) compared to the control without biocatalyst, indicating higher amount of $CO_2$ conversion in presence of biocatalyst (Table 3). Commercial carbonic anhydrase evaluated in the present experiment did not showed higher carbonate production. The TEM analysis of carbonates showed the size of particle in range of 50-100 nm in presence of biocatalyst developed in this invention while it was irregular and more than 500 nm without biocatalyst and other carbonic anhydrase (CAs).

TABLE 1

Composition of the spent caustic

| Component | Wt % |
|---|---|
| NaOH | 3 |
| Sulphide | 1.67 |
| Mereaptide | 2.9 |
| Cresylic acids | 6 |
| Naphthenic acids | 3 |
| Phenol | 0.018 |
| Hydrocarbon | 0.3 |
| pH | 14 |

TABLE 2

Composition of the brine

| pH | 8 |
|---|---|
| TDS | 6000 ppm |
| TSS | 18857 ppm |
| O&G | 300 ppm |
| Hardness | 1400 ppm |
| Total Alkalinity | 125 ppm |
| $Ca^{2+}$ | 1200 ppm |
| $Mg2+$ | 589 ppm |

TABLE 3

Carbonates formation under different experimental conditions in 5 minutes

| Test conditions | Carbonate as precipitated (g) | Size of the carbonate |
|---|---|---|
| Carbonic anhydrase from *Bacillus thermoleovorans* (MTCC 25023) | 118.2 ± 6.56 | 50-100 nm |
| Carbonic anhydrase from bovine | 39.67 ± 2.45 | 500-600 nm |

TABLE 3-continued

Carbonates formation under different experimental conditions in 5 minutes

| Test conditions | Carbonate as precipitated (g) | Size of the carbonate |
|---|---|---|
| Carbonic anhydrase from Human | 30.7 ± 2.23 | 500-600 nm |
| Control (no biocatalyst) | 26.3 ± 1.67 | 500-600 nm |

Treatment of Aqueous Phase

The aqueous phase decanted from precipitated carbonates and their washing contained the sulphides, phenols, hydrocarbons, etc. The aqueous phase after carbonate precipitation was introduced in the reactor having collected the volatile compounds. It was treated using a microbial consortia developed in the present invention. A microbial consortium comprising of *Pseudomonas putida* (MTCC 5869), *Bacillus substilis* MTCC 5386, *Pseudomonas aeruginosa* (MTCC 5389), *Peudomonas aerugiosa* (MTCC 5388), *Lysinibacillus* sp. (MTCC 5666) was prepared and evaluated CSTR with air bubbling system. Treatment is done in batch mode. The residual liquid after carbonate precipitation was fed in the reactor. Along with nutrient system comprising of 4 g/l $K_2HPO_4$, 4 g/l $KH_2PO_4$, $MgCl_2$ 0.2 g/l, 0.5 g/l of trace elements, 2 g/l Urea 5 g/l yeast extract, 4 g/l sodium nitrate. The pH and temperature was not maintained. The percentage of oxygen saturation was controlled 100%. The stirring was done 600 rpm. To prevent the release of volatile compounds from the system, gas phases were continuously recycled. The recycled gas first passed to a condenser (maintained at 5° C.) to recover the volatile compounds and metabolites. An abiotic control with similar conditions was also operated. At the time interval samples were taken and were analyzed for CFU/ml on agar plate as well for concentration of contaminant by suitable analytical techniques. In batch mode, after 24 hours, the treated spent caustic has more than 98% reduction in total sulfur, sulphides, mercaptans, hydrocarbon, phenol and other contaminants in comparison to abiotic control without the microbial consortia (Table-4). The treated reactor was having >$10^{12}$ cfu/ml in comparison to $10^2$ in abiotic reactor. Once, the contaminant reduced to substantial level, the treated spent caustic is removed and biomass is recovered. The recovered biomass is recycled and used for treatment fresh aqueous layer of spent caustic after sparging $CO_2$ in presence of carbonic anhydrase.

TABLE 4

Treatment of aqueous phase

| | wt % (% degradation) after 24 hrs | |
|---|---|---|
| Contaminant | Treated with microbial blend | Control without microbial blend |
| Total sulfur | 0.02 (98.3) | 2.89 (1.4) |
| Sulphides | 0.03 (98.6) | 1.62 (2.4) |
| Mercaptans | 0.017 (99.4) | 2.72 (5.9) |
| Phenol | 0.0002 (98.8) | 0.017 (2.5) |
| Hydrocarbons | 0.0006 (99.8) | 0.29 (1.7) |

Example-2

The carbonic anhydrase obtained from *Bacillus thermoleovorans* (MTCC 25023) nickel ferrite. Nickel ferrite nanoparticles were synthesized via co-precipitation method. Typically, 0.4 M (25 mL) solution of iron chloride ($FeCl_3$) and a 0.2 M (25 mL) solution of nickel chloride ($NiCl_2$) in deionized water were mixed with vigorous stirring. 0.1 g of tannic acid or Polyethylene glycol was added to it and the temperature was raised to 80° C. 3 M NaOH solution was added drop wise till the pH reached to ~12. The brown precipitate obtained was filtered and dried in oven for 24 h. The solid $NiFe_2O_4$ obtained is then calcined at 600° C. for 4 h and stored at room temperature. $ZnFe_2O_4$ was synthesized using the similar procedure with $ZnCl_2$ (0.2 M, 25 mL) as zinc precursor. The immobilization of carbonic anhydrase (CA) was carried out on $NiFe_2O_4$ and $ZnFe_2O_4$ by ionic adsorption. 0.5 g of $NiFe_2O_4$ or $ZnFe_2O_4$ was ultrasonicated for 10 min using 5 ml of Trisbuffer (pH=8). After sonication 5 ml CA (1 mg/ml) was added and slowly stirred for 30 min. The solution is then centrifuged and the supernatant are tested for enzyme concentration. The solid is stored at ~4° C. for further application.

The 1 L refinery spent caustic and 1 L brine solution obtained from crude desalting process were mixed in a stirred reactor along with biocatalyst (20 mg). To this, industrial flue gas was sparged (2 L/min) for 10 minutes at ambient temperature (65° C.). To prevent the release of volatile compounds from the system, gas phases were continuously recycled. The recycled gas first passed to a condenser (maintained at 5° C.) to recover the volatile compounds and condensate was collected in another reactor. This results in the precipitation of metal carbonates. A control without biocatalyst and commercially available biocatalyst i.e., carbonic anhydrase from bovine serum (Purchased from Sigma) and human carbonic anhydrase-II (purchased from Sigma) was also kept under same experimental conditions. The precipitate obtained was separated and washed. It was analyzed for its composition by XRF, XRD and for size and shape of particles by TEM. Table-5 showed the results.

TABLE 5

Calcium carbonates formation in 5 minutes

| Test conditions | Carbonate as precipitated (g) | Size of the carbonate |
|---|---|---|
| Enzyme from *Bacillus thermoleovorans* (MTCC 25023) immobilized on nickel ferrite | 158.2 ± 3.51 | 50-100 nm |
| Carbonic anhydrase, bovine immobilized on nickel ferrite | 40.47 ± 2.65 | 500-650 nm |
| Carbonic anhydrase, Human immobilized on nickel ferrite | 35.7 ± 1.83 | 500-600 nm |
| Control (no biocatalyst, only nickel ferrite) | 36.2 ± 1.67 | 500-660 nm |

The microbes of Table 6 having the deposit (accession) number and date of deposit were deposited with the Microbial Type Culture Collection (MTCC), Chandigarh, India having an address of: Institute of Microbial Technology, Shanti Path, 39A, Sector 39, Chandigarh, 160036, India. All restrictions on the availability to the public of the material so deposited will be irrevocably removed upon granting of this patent.

TABLE 6

| Deposits | Date of Deposit/Acceptance |
|---|---|
| *Enterobacter aerogenes* (MTCC 25016) | 9 Apr. 2015 |
| *Lysinibacillus* sp. (MTCC 25029) | 20 Apr. 2015 |
| *Bacillus thermoleovorans* (MTCC 25023) | 10 Apr. 2015 |
| *Bacillus stearothermophilus* (MTCC 25030) | 20 Apr. 2015 |

TABLE 6-continued

| Deposits | Date of Deposit/Acceptance |
|---|---|
| *Arthrobacter* sp. (MTCC 25028) | 20 Apr. 2015 |
| *Pseudomonas putida* (MTCC 5869) | 11 Oct. 2013 |
| *Bacillus substilis* (MTCC 5386) | 17 Dec. 2007 |
| *Pseudomonas aeruginosa* (MTCC 5389) | 17 Dec. 2007 |
| *Pseudomonas aerugiosa* (MTCC 5388) | 17 Dec. 2007 |
| *Lysinibacillus* sp. (MTCC 5666) | 12 Oct. 2011 |

We claim:

1. A process of converting refinery waste streams comprising spent caustic into nano-sized carbonates, comprising the steps of:
   (a) mixing the refinery waste stream comprising spent caustic in a stirred reactor containing carbonic anhydrase, which is obtained from the microbe selected from *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028);
   (b) adding a brine solution to the mixture of step (a);
   (c) sparging a carbon dioxide rich gas to the mixture of step (b);
   (d) allowing the components introduced in (a)-(c) to react for a sufficient time and at a sufficient concentration to form a nano-sized carbonate precipitate;
   (e) separating the aqueous/liquid phase to obtain precipitated nano-sized carbonate;
   (f) treating the aqueous/liquid phase with a microbial consortia selected from a mixture of any one of *Pseudomonas putida* (MTCC 5869), *Bacillus substilis* (MTCC 5386), *Pseudomonas aeruginosa* (MTCC 5389), *Peudomonas aerugiosa* (MTCC 5388) and *Lysinibacillus* sp. (MTCC 5666) for a sufficient time and at a sufficient concentration to remove contaminants; and
   (g) obtaining a aqueous phase free of contaminants.

2. The process as claimed in claim 1, wherein the carbonic anhydrase is at a concentration in the range of 2-20 units/ml of the reaction mixture and is capable of withstanding: i) a pH above 10, ii) salinity in the range of 0.1-10% and iii) temperatures above 80° C.

3. The process as claimed in claim 1, wherein the source of carbon dioxide rich gas is selected from flue gas or bio-gas plant exhaust.

4. The process as claimed in claim 1, wherein the brine solution is obtained from sources selected from crude oil-desalter unit, produced water, reverse osmosis plant reject, or cooling tower blow down.

5. The process as claimed in claim 1, wherein the ratio of spent caustic in the refinery waste stream and brine solution is in the range of 1:1 to 1:0.10.

6. The process as claimed in claim 1, wherein the process in steps (a) to (d) are carried out at a temperature in the range of 25-85° C. for 0.5-30 minutes.

7. The process as claimed in claim 1, wherein the carbonic anhydrase may be immobilized in the immobilization agents selected from carbon nanotubes, metal organic framework, zeolites, Zinc-ferrite, nickel ferrite, Zinc-nickel (Zn—Ni) ferrite, polyurethane, glass beads or any other suitable matrixes.

8. The process as claimed in claim 1, wherein step (f) is carried out at a temperature in the range of 20-60° C. and stirring of the reaction is carried in range of 200-600 rpm.

9. The process as claimed in claim 1, wherein the total dissolved solids in brine solution in the range of 10 ppm to 100000 ppm.

10. The process as claimed in claim 1, wherein the nano-sized carbonate has a particle size in the range of 50-100 nm.

11. The process as claimed in claim 1, wherein the treated aqueous/liquid phase or the spent caustic has more than 98% reduction in sulphides, phenols, hydrocarbons, naphthenic acid, thiols, mercaptans or other contaminants.

12. A process of converting refinery waste streams comprising spent caustic into nano-sized carbonates, said process comprising the steps of:
 (a) mixing the refinery waste in a stirred reactor containing carbonic anhydrase, wherein the carbonic anhydrase is obtained from microbes selected from *Enterobacter aerogenes* (MTCC 25016), *Lysinibacillus* sp. (MTCC 25029), *Bacillus thermoleovorans* (MTCC 25023), *Bacillus stearothermophilus* (MTCC 25030) or *Arthrobacter* sp. (MTCC 25028);
 (b) adding a brine solution to the mixture of step (a);
 (c) sparging a carbon dioxide rich gas to the mixture of step (b);
 (d) allowing the components introduced in (a)-(c) to react for a sufficient time and at a sufficient concentration to form a nano-sized carbonate precipitate; and
 (e) recovering precipitated nano-sized carbonates.

13. The process as claimed in claim 12, wherein the carbonic anhydrase is at a concentration in the range of 2-20 units/ml of the reaction mixture and is capable of withstanding: i) a pH above 10, ii) salinity in the range of 0.1-10% and iii) temperatures above 80° C.

14. The process as claimed in claim 12, wherein the source of carbon dioxide rich gas is selected from flue gas or bio-gas plant exhaust.

15. The process as claimed in claim 12, wherein the brine solution is obtained from sources selected from crude oil-desalter unit, produced water, reverse osmosis plant reject or cooling tower blow down.

16. The process as claimed in claim 12, wherein the ratio of spent caustic in the refinery waste stream and brine solution is in the range of 1:1 to 1:0.10.

17. The process as claimed in claim 12, wherein the process in steps (a)-(d) are carried out at a temperature in the range of 25-85° C. for 0.5-30 minutes.

18. The process as claimed in claim 12, wherein the biocatalyst in steps (a)-(d) may be immobilized in the immobilization agents selected from carbon nanotubes, metal organic framework, zeolites, Zinc-ferrite, nickel ferrite, Zinc-nickel (Zn—Ni) ferrite, polyurethane, glass beads or any other suitable matrixes.

* * * * *